United States Patent [19]
Kokish

[11] Patent Number: 5,704,898
[45] Date of Patent: Jan. 6, 1998

[54] ARTICULATION MECHANISM FOR AN ENDOSCOPE

[75] Inventor: Arkady Kokish, Orange, Conn.

[73] Assignee: Circon Corporation, Santa Barbara, Calif.

[21] Appl. No.: 560,436

[22] Filed: Nov. 17, 1995

[51] Int. Cl.$^6$ ..................................................... A61B 1/00
[52] U.S. Cl. .......................... 600/141; 600/139; 600/142; 600/146; 600/152
[58] Field of Search .................. 600/139, 141–142, 600/146–147, 152

[56] References Cited

U.S. PATENT DOCUMENTS

| | | | |
|---|---|---|---|
| 3,270,641 | 9/1996 | Gosselin | 600/142 X |
| 3,557,780 | 1/1971 | Sato | 600/141 |
| 3,799,151 | 3/1997 | Fukaumi et al. | 600/142 |
| 4,790,294 | 12/1988 | Allred III, et al. | 600/141 |
| 4,873,965 | 10/1989 | Danieli | 600/141 |
| 5,105,819 | 4/1992 | Wollschläger et al. | 600/152 X |
| 5,174,277 | 12/1992 | Matsumaru | 600/142 |
| 5,178,129 | 1/1993 | Chikama et al. | 600/142 |
| 5,179,935 | 1/1993 | Miyagi | 600/142 |
| 5,181,514 | 1/1993 | Solomon et al. | 600/152 X |
| 5,271,382 | 12/1993 | Chikama | 600/142 |

Primary Examiner—Beverly M. Flannagan
Attorney, Agent, or Firm—Daniel J. Meaney, Jr.

[57] ABSTRACT

An articulation mechanism for an endoscope wherein the endoscope has a generally elongated shaft and cables extending between a control head located at the proximal end thereof and an objective assembly located at the distal end thereof wherein the objective assembly is capable of being deflected over an arcuate co-planar path by the articulation mechanism is shown. The articulation mechanism comprises a proximal ring having a first outer edge and a second outer edge and the proximal ring is operative coupled to the distal end of the endoscope at one of the first outer ring and second outer ring and having a coupling member defined on the other of the first outer ring and second outer ring. A central ring having a first outer edge and a second outer edge, each of which defines an actuation member, is operatively connected by one of the actuation members to the coupling member. A distal ring having a first outer edge defining a coupling member a second outer edge wherein the second coupling member is operatively coupled to and which cooperates with the other of the actuation members. The central ring and the distal ring are operatively coupled to the cables and are responsive to the direction of movement of the cables to sweep the objective assembly over an arcuate co-planar path defined by a first predetermined angular path and a second predetermined angular path.

21 Claims, 7 Drawing Sheets

ARTICULATION MECHANISM FOR AN ENDOSCOPE

BACKGROUND OF THE INVENTION

1. Description of the Invention

The invention relates to an articulation mechanism for an endoscope wherein the endoscope has a generally elongated shaft extending between a control head and an objective assembly and more particularly relates to an articulation mechanism having a proximal ring, central ring and distal ring which is responsive to direction of movement of cables within the endoscope to sweep the objective assembly over an arcuate coplanar path.

2. Description of the Prior Art

Endoscopes are well-known in the art. Typically, endoscopes are optical imaging devices used for viewing objects within cavities or the internal surface of cavities. Certain endoscopes have working channels for insertion of devices or weakening tools or surgical instruments to act upon or treat conditions within an operative site.

While the herein described invention has application in many fields, it has particular relevance to the medical field wherein flexible endoscopes having an articulation section are employed to view and treat deep and convoluted passages of the human body. Optical images transferred within the endoscope by image transferring systems are usually applied to video cameras to produce video images for the operator to view during a procedure.

Endoscopes are also used with ultrasonic transducers mounted at the distal end. Such endoscopes are inserted through the trachea and into the lungs. The distal end of the endoscope is then mechanically sweeps across an operative site to generate an ultrasonic image of an area, such as, for example, the heart. This procedure is generally referred to as Transesophageal Electrocardiogram ("TEE").

In a typical endoscope designed for such purposes, the distal tip of the instrument is made maneuverable by employing two or more angularly spaced cables which interact mechanically with a series of vertebrated or specifically profiled rings located adjacent to the distal end of the instrument. This is sometimes referred to as an articulation mechanism. Bending and deflection of the rings are obtained by tensioning and relaxing the cables in accordance with controls located at the proximal end of the endoscope on the control head. The means for applying tension and relaxing forces to these cables have been the subject of extensive technological effort resulting in controls such as coaxial control wheels found on many well-known endoscopes. The object of these efforts has been to provide on the control head of the endoscope cable tensioning and relaxing means accessible and comfortable to the hands and fingers of the operator, and, consistent with holding the scope, operating all other controls, and allowing such other manipulations of the endoscope (i.e., torque, pushing and pulling) as are deemed effective for the clinical procedure for which the endoscope was designed.

A typical multi lumen core deflecting endoscope is disclosed in U.S. Pat. No. 4,798,969. A cable compensation mechanism adapted for use with endoscopes having an articulation mechanism is disclosed in U.S. Pat. No. 4,688,555. The compensation mechanism engages the cables intermediate their ends and is effective to guard the cable against excessive loads and also to readily accommodate variations in the working length of the cables as occurs when the cable are permanently stretched.

Throughout this disclosure, it will be appreciated that the term "cable" is intended to refer to any elongate material which can be effectively utilized to operatively connect the distal end of the instrument including the articulation mechanism to the control head. Thus, for purposes of the invention, wire, bands, chains and the like are considered to be equivalent to cables. The term "operating cable and sheath assembly" refers to an assembly comprising a cable located with a sheath wherein the cable moves within the sheath.

In TEE procedures, the distal tip of the endoscope could become internally restrained by contacting tissue or bone within the cavity during the procedure. In such event, the cable could be subject to a high tensile force or could break. If the distal tip is in a curved or deflected position and mechanically becomes fixed in the deflected position, it becomes difficult to remove the endoscope from a patient.

A factor to be considered in the construction of the endoscope for its normal medical use is its flexibility and articulation which permits the objective tip to be directed along a selected passageway such as in the trachea or in the urinary tract. An endoscope can be made to traverse a considerable distance within the selected passageway providing that any bends in the channel have a sufficiently large radius of curvature to enable the objective assembly of the endoscope to be readily articulated to follow the course of the passageway. Care must be taken, however, to precisely guide the instrument so as not to puncture any cavity or passageway walls such as the vesical wall, especially as the device is being inserted.

Endoscopes are also used for inspecting mechanical structures requiring elongated tubular inspection devices. Typically, such endoscopes incorporate flexible fiber optics including a fiber optic image bundle. One application is to inspect the first stage or high temperature stage of a jet engine just behind the burner in that such components are most subject to wear and deterioration. The arrangement of the jet engine's rotor and starter blades, particularly those in the high temperature state of the engine, presents a most complex geometry which has not been amenable to inspection in the past other than by first disassembling the engine.

While the state-of-the-art relating to endoscopes is relatively advanced today, there are still recurring problems which result when excessive stresses are applied to the operating cables by the hand operated control mechanism. In an extreme situations, this can result in breakage of the cable or, in a less extreme situation, to permanently stretching of the cable. In the former instance, then endoscope is rendered useless until the cable has been replaced. In a latter instance, the endoscope loses a portion of its original deflection capability, making it necessary to take up the slack of the stretched cable and to recalibrate the instrument. In both instances, it is necessary to repair the instrument to its former operating condition. This procedure, of course, results in considerable downtime thereby creating scheduling problems, possibly delaying for long periods of time critical inspection procedures which cannot be performed until the instrument has been repaired.

One TEE probe presently offered for sale and manufactured by the assignee of this invention is described in a United States patent application entitled RATCHET CONTROL MECHANISM FOR AN ENDOSCOPE assigned Ser. No. 08/330,314 filed Oct. 24, 1994, also assigned to the same assignee, utilizes a control mechanism which is operatively connected to the operating cable and sheath assembly within the control head for moving the operating cable within the sheath to deflect the objective assembly. The control mechanism is adapted to control the magnitude of tensile force developed in the operating cable in the event that deflection of the objective assembly is restrained. The control mechanism has a guide block and carriage member moveable therein wherein the moveable carriage member is operatively connected to the operating cable and sheath assembly. The guide block includes a first resilient member positioned between the moveable carriage member and the guide block. The first resilient member is capable of being compressed between the moveable carriage member and guide block when the tensile force on the operating cable reaches a first predetermined value. The guide member includes a second resilient member which is operatively connected between the operating cable and sheath assembly and the moveable carriage member and which is adjacent to the first resilient member. The second resilient member restrains movement of the carriage member when the tensile force is below the predetermined value. When the tensile force reaches at least the predetermined value, the second resilient member is responsive to absorb the tensile force in excess of the predetermined value and release the carriage member. The carriage member moves the sheath within the guide block to prevent the tensile force from being applied to and impairing the operating cable and sheath assembly.

A typical endoscope articulation mechanism consists of hoop-shaped "rings." A proximal ring is anchored to the distal end of the endoscope shaft. Wire cables string the proximal ring and other rings including a distal ring together to work as an articulation assembly. Two cables, 180° apart are needed to 2-way deflection. Four cables 90° apart are needed for 4-way deflection. The cables are connected only to the distal ring and the deflection control mechanism. Pulling on one cable causes deflection in one direction. There are various known means to create cable linear motion and to control the deflection. For example, the endoscope shaft may be 12 mm diameter and is operatively attached to a handle having two control knobs. This particular probe is capable of 4 -way deflection. The plane described by up/down deflection sweep contains the forces that arise due to acoustic coupling. The orthogonal plane contains the forces that arise due to organ lifting. The inability to maintain smooth deflection mechanism curvature under load is inherent in the design of the prior art deflection mechanism. The lack of shape stability detracts from the usefulness of the endoscope. Optical endoscopes are used extensively in laparoscopic surgery. Surgeons use the optical images for diagnostic and therapeutic procedures. However, the optical view stops at the surface of the organs or tissue under treatment.

Ultrasound imaging is a modality used to generate "views" beneath the surface of the organ. An endoscope designed for such imaging has an ultrasound transducer located at the distal end of the articulation mechanism. The ultrasound transducer is placed directly on the organ or tissue to be imaged. The image is transmitted via electrical wires which pass through the shaft and exit at the distal end of the handle. A computer reconstructs the image on a CRT screen.

Articulation mechanisms designed for ultrasound laparoscopy must meet the following three parameters:

A. Acoustic coupling with the imaged organ is critical. The physician must be able to accurately place the ultrasound transducer surface directly on the organ or tissue with some pressure.

B. The articulation mechanism of the laparoscope or endoscope must be capable of lifting organs so as to access the target to be imaged. The articulation mechanism must have sufficient mechanical strength to provide the necessary lifting forces to lift organs or tissue to gain access to the desired target area.

C. The articulation mechanism must be sealable with an elastomeric boot to create electrical isolation.

SUMMARY OF THE INVENTION

A new, novel and unique articulation mechanism for an endoscope for performing diagnostic or medical procedures is disclosed and taught by the present invention. In the preferred embodiment, the endoscope includes an articulation mechanism which comprises a first ring which is adapted to be operatively connected to an end of a hollow elongated shaft of an apparatus. The first ring has a coupling member formed thereon and is positioned in a spaced relationship to the end of a shaft. The articulation mechanism further includes a first drive ring having first and second actuation members positioned in a spaced opposed relationship and wherein one of the first and second actuation members is operatively coupled to the coupling member. The first drive ring includes a first cable connecting member for operatively connecting the first drive ring to a first pair of moveable cables for rotating, in response to the direction of movement of a first pair of cables, the first drive ring over a first arcuate path. The articulation mechanism includes a second drive ring having a second coupling member formed thereon which is operatively coupled to the other of said first an second actuation members. The second drive ring includes a second cable connecting member for operatively connecting the drive ring to a second pair of moveable cables for rotating, in response to the movement of a second pair of cables, the second drive ring over a second arcuate path which is co-planer with the first arcuate path. The articulation mechanism may further include a first idle ring operatively coupled between the coupling member of the first drive ring and one of the first and second actuation members of the first drive ring. In addition, the articulation mechanism may include a second idle ring operatively coupled between the second coupling member of the second drive ring and the other of the first and second actuation members of the first drive ring.

In the preferred embodiment, the articulation mechanism can be used as a robotic surgical finger for an endoscope.

One advantage of the present invention is that the articulation mechanism can be located at the distal end of an endoscope and can be used for performing various surgical procedures.

Another advantage of the present invention is that the articulation mechanism can be used as a robotic surgical finger.

Another advantage of the present invention is that an endoscope having the articulation mechanism can be used as an optical endoscope or as an endoscope for use with an ultrasonic transducer.

Another advantage of the present invention is that an endoscope using the articulation mechanism can have the distal end thereof deflected under a load.

Another advantage of the present invention is that the articulation mechanism can be used at the distal end of an endoscope and can be used to lift or move organs in a body to provide access to an operative site.

Another advantage of the present invention is that an endoscope having the articulation mechanism may include a control mechanism to move a first and second cable pair in a selected direction and a predetermined distance to cause the distal end of the articulation mechanism to be deflected over a coplanar arcuate shaped path.

Another advantage of the present invention is that an endoscope having an articulation mechanism of the present invention can be used for performing a variety of surgical procedures.

Another advantage of the present invention is that each ring or drive ring is a stiff, rigid element and when formed into an assembly, the assembly is flexible and can be formed into predetermined angles or shapes.

Another advantage of the present invention is that the robotic surgical finger can be deflected into a predetermined angle having a predetermined shape or can be deflected into one or more angles to form a selected shape for performing a procedure. In addition, when the articulation mechanism is deflected into a selected angle or shape, if the articulation mechanism is subject to a pulling or pushing force exerted exterior to the articulation mechanism, the articulation mechanism will retain the deflected angle and/or shape under such loading conditions.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Figure 1:
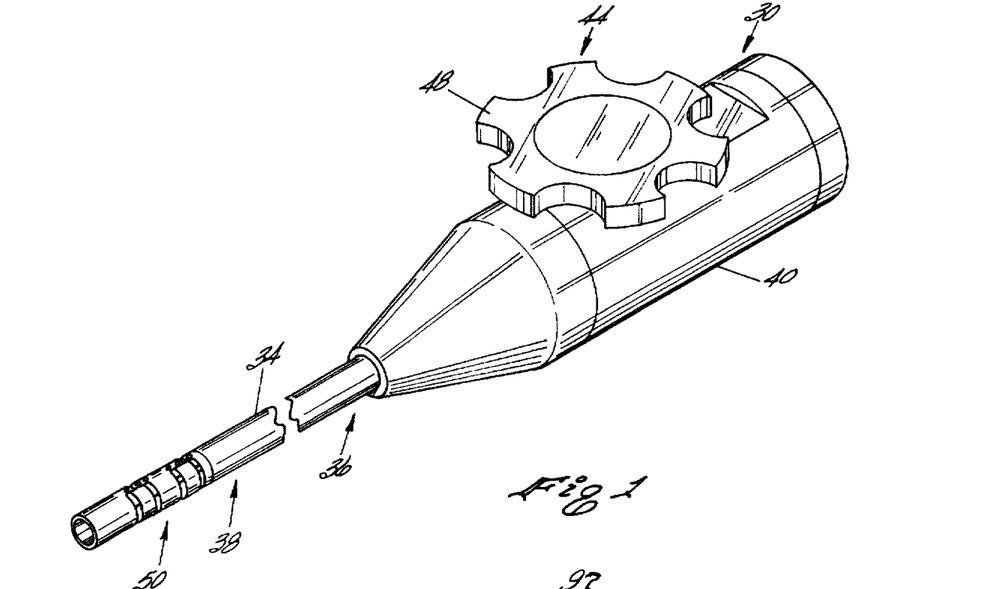
FIG. 1 is a top, front and left side perspective view of a endoscope having an articulation mechanism subject of the present invention.

FIG. 1 illustrates an apparatus having a hollow elongated shaft, which in the preferred embodiment, is an endoscope shown generally as 30. The endoscope 30 includes a hollow elongated shaft 34 having a proximal end shown generally as 36 and a distal end shown generally as 38. The proximal end 36 of the hollow elongated shaft 34 has a control head 40 operatively connected thereto. The control head 40 includes a cable drive mechanism shown generally as 44 in the form of a hand ring shown as 48.

The distal end 38 of the hollow elongated shaft 34 includes an articulation mechanism shown generally as 50.

Figure 2:
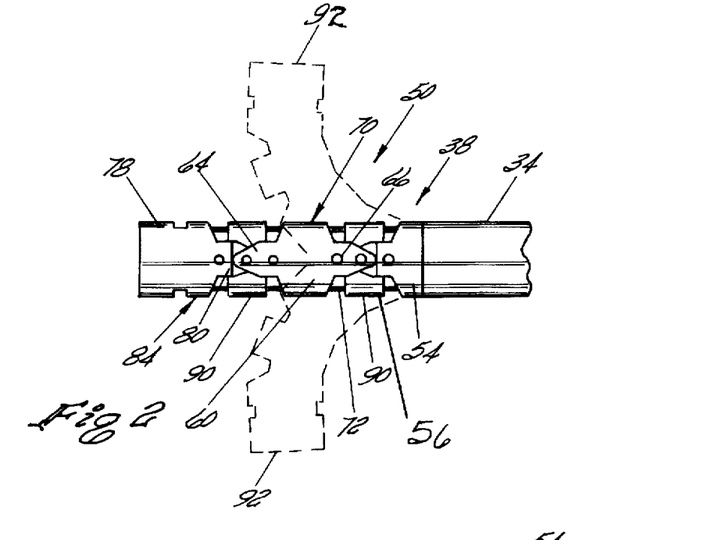
FIG. 2 is a partial top plan view of the distal end of an endoscope incorporating the articulation mechanism illustrated in FIG. 1 and subject of the present invention and showing in phantom lines to deflected position of the distal end of the articulation mechanism.

FIG. 2 shows in greater detail the structure of the articulation mechanism 50 which is operatively connected to the distal end 38 of the hollow elongated shaft 34. The articulation mechanism 50 has a first ring 54 which is adapted to be fixedly operatively connected to the distal end 38 of the hollow elongated shaft 34. In FIG. 2, the first ring 54 is a separate element which is mechanically attached to the distal end 38 of the shaft 34. The first ring 54 has a coupling member 56 formed thereon and positioned in a spaced relationship to the end of the shaft 34.

A first drive ring 60 has first and second actuation members 64 and 66 positioned thereon in a spaced opposed relationship. One of the first and second actuation members 64 and 66 which are elongated support members as shown in FIG. 2, is operatively coupled, in the preferred embodiment pivotally coupled to the coupling member 56. In FIG. 2, actuation member 66 is illustrated as being pivotally coupled to the coupling member 56. The first drive ring 60 includes a first cable connecting member shown generally as 70 for operatively connecting the first drive ring 60 to a first pair of movable cables 72. The first pair of moveably cables 72 are used for pivoting, in response to the direction of movement of the first pair of cables 72, the first drive ring 60 over a first arcuate path.

FIG. 2 shows a second drive ring 78 or second drive element having a second coupling member 80 formed thereon which is operatively coupled, which in the preferred embodiment is pivotally coupled to the other of the first and second actuation members 64 and 66. The second drive ring 78 includes a second cable connecting member shown generally as 84 for operatively connecting said second drive ring 78 to a second pair of cables 88, shown in FIG. 5. The second pair of moveably cables 88 are used for pivoting in response to the movement of a second pair of cables 88, the second drive ring 78 over a second arcuate path which is co-planar with the first arcuate path.

FIG. 2 shows, in phantom, illustrated by dashed line 92, the articulation mechanism 50 as deflected over a first arcuate path.

FIG. 2 also shows, in phantom, illustrated by dashed line 92', the articulation mechanism 50 as deflected over a second arcuate path.

Figure 3:
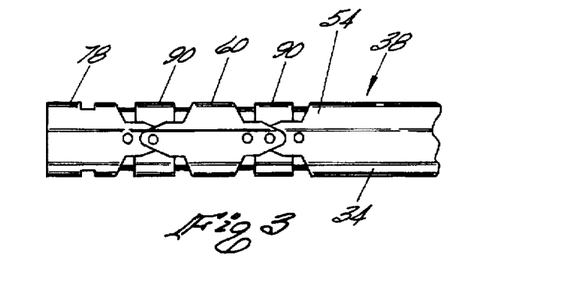
FIG. 3 is a top plan view of the articulation mechanism operatively connected on the end of an endoscope housing.

FIG. 3 shows the same articulation mechanism of FIG. 2 except that the first ring 54 is formed to be integral with the distal end 38 of the hollow elongated shaft 34. In both FIGS. 2 and 3, a pair of idle rings 90 or first and second idle ring, respectively, are shown to be positioned intermediate the first ring and first drive ring or the first drive ring the second drive ring.

Figure 4:
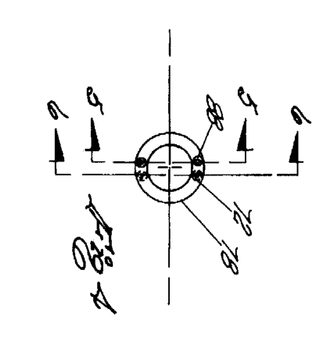
FIG. 4 is a left side elevational view of the articulation mechanism of FIG. 3.

FIG. 4 is an end view showing in greater detail the structure of the second drive ring 78. The cables 72 and 88 are shown in FIG. 4.

Figure 5:
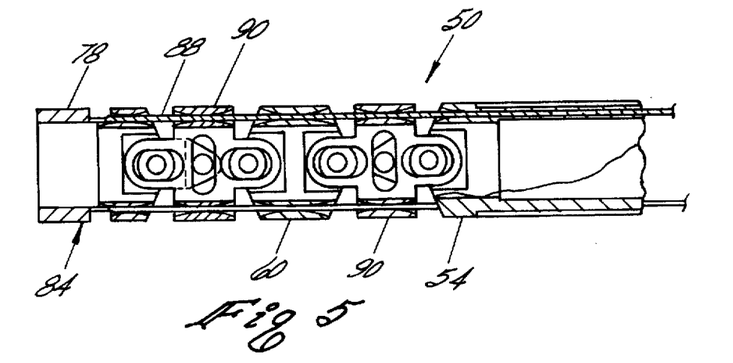
FIG. 5 is a sectional view of the distal end of the articulation mechanism taken along section line 5—5 of FIG. 4.
Figure 6:
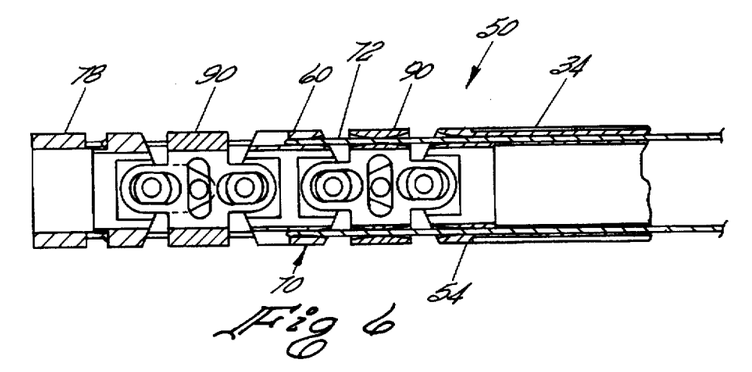
FIG. 6 is a sectional view of the distal end of the articulation mechanism taken along section lines 6—6 of FIG. 4.

FIGS. 5 and 6 show in cross-section the details of the articulation mechanism 50 and the locations of the cables 72 and 88 therein. In FIGS. 5 and 6, each of the idle rings and the ring or drive rings have a first outer edge and a second outer edge defining an opening having a constriction or throat between two tapered sections forming opposed cable supporting surfaces defining spaced curved openings which receive and pass the cables 72 and 88. In FIG. 5, the second cable connecting member 84 terminates the second pair of cables 88 within the second drive ring 78. In FIG. 6, the first cable connecting member 70 operatively connects the first pair of cables 72 to the first drive ring 60.

Figure 7:
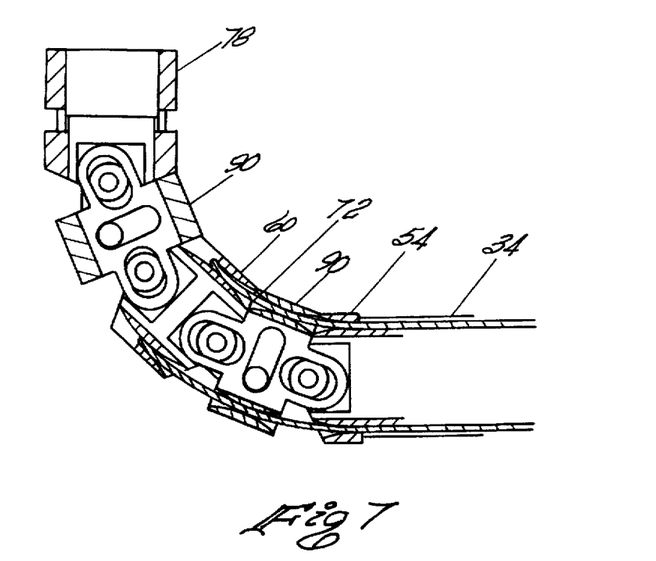
FIG. 7 is a partial cross-sectional view of the articulation mechanism having two idle rings deflected about 90° along a first arcuate path.

FIG. 7 shows the articulation mechanism of FIG. 6 showing the bending of the first pair of moveably cables 72 and that the cable contacts and is supported by the inner surface of one of the outer edges of the first idle ring 90 and/or first ring 54.

Figure 8:
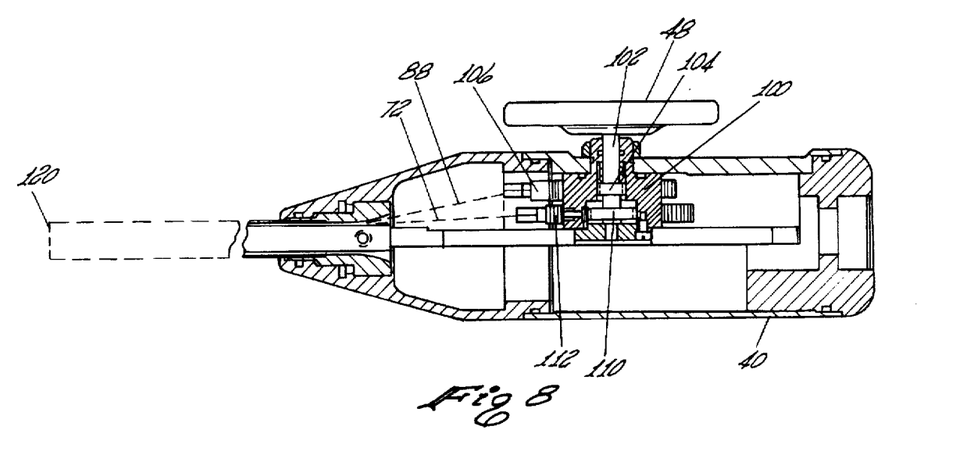
FIG. 8 is a partial cross-sectional view of the proximal end of an endoscope having a housing for enclosing a control mechanism and showing the distal end in phantom.

FIG. 8 shows in cross-section the cable compensation mechanism of the preferred embodiment which is internal to the control head 40. The cable mechanism includes the hand wheel 48 also known as a drive member which has a shaft 102 having drive gears 104 and 110 also known as a first and second co-acting member, which co-act with driven members 106 and 112 also known as a reactive member or linear geared rack member. A housing 100 encloses the driven members 106 and 112. The first pair of moveable cables 72 and second pair of moveable cables 88 are fixedly connected to their appropriate driven members 106 and 112. In FIG. 8, the articulation mechanism could include an ultrasonic transducer 120. Movement of the articulation mechanism results in the ultrasonic transducer being transported over the arcuate paths by the articulation mechanism adjacent to an operative site to produce an ultrasound image thereof.

FIGS. 9 through 12 shown an alternative embodiment of the articulation mechanism without any idle rings. As illustrated in FIG. 13, the deflection of the second pair of moveable cables 88 is not supported intermediate the fixed ring 54 and the drive rings 60 and 78.

Figures 9, 10, 11, 12, 13, 14:
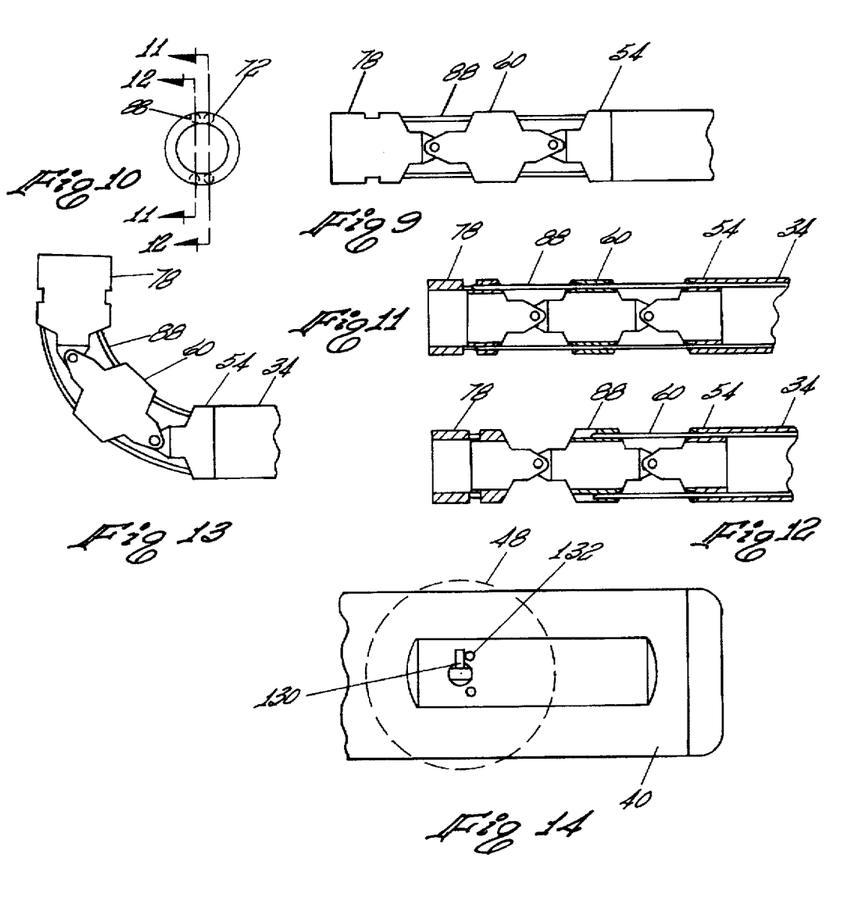
FIG. 9 is a top plan view of another embodiment of an articulation mechanism having a first element, a first drive element and a second drive element.
FIG. 10 is a left end plan view of the articulation mechanism of FIG. 9.
FIG. 11 is a sectional view taken along section lines 11—11 of FIG. 10 showing the second pair of cables operatively connected to the second drive ring.
FIG. 12 is a sectional view taken along lines 12—12 of FIG. 11 showing a first pair of cables operatively connected to the first drive ring.
FIG. 13 illustrates pictorially the articulation mechanism of FIG. 9 deflected about 90° over a first arcuate path.
FIG. 14 illustrates pictorially a control mechanism having an external stud to limit the angle of deflection of the articulation mechanism to 90°.

FIG. 14 illustrates diagramatically that the control head 40 can include a member 130 which operates as a mechanical stop to limit the rotation of the hand wheel 48 such that the member 140 by engaging stop 142 limits the deflection to a predetermined angle such as, for example, 90°.

Figures 15A, 15B, 15C:
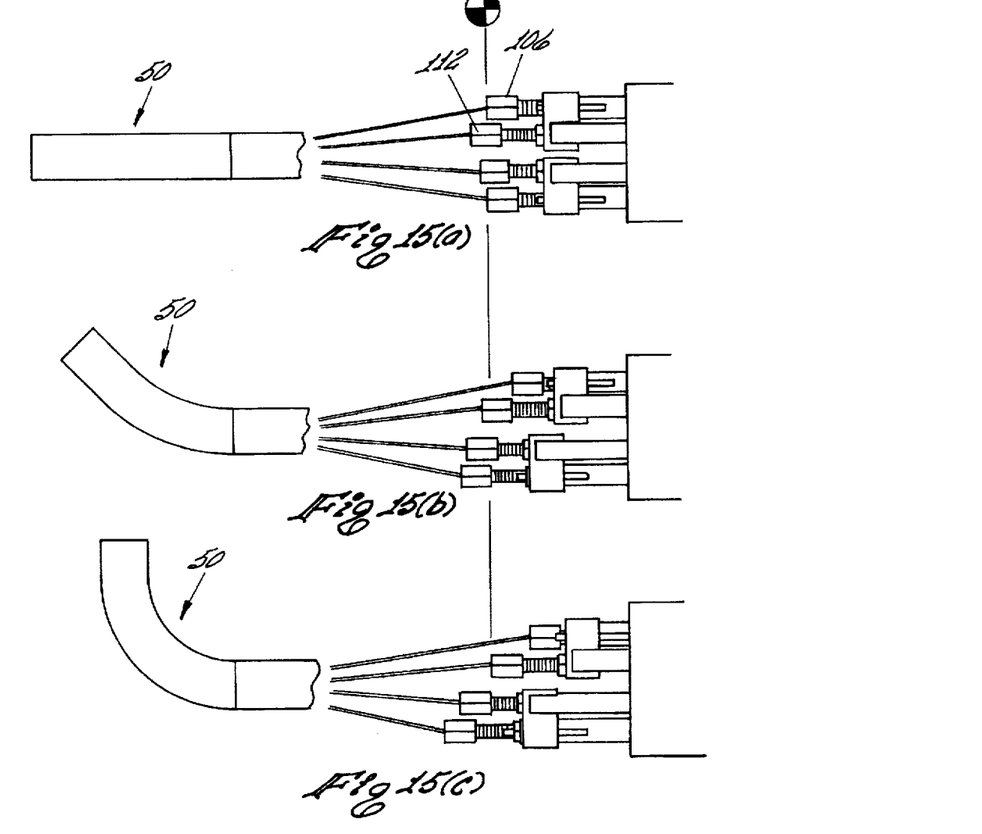
FIG. 15(a), FIG. 15(b) and FIG. 15(c) illustrate the position of the drive member and driven member when the articulation mechanism is substantially in line with the center axis of the endoscope, is deflected partially along a first arcuate path and deflected approximately 90° deflection along the same arcuate path, respectively.

FIG. 15(a), FIG. (b) and FIG. 15(c) illustrate the relationship between the driven members 106 and 112 for deflecting the articulation mechanism 50 over an arcuate path.

Figures 16, 17:
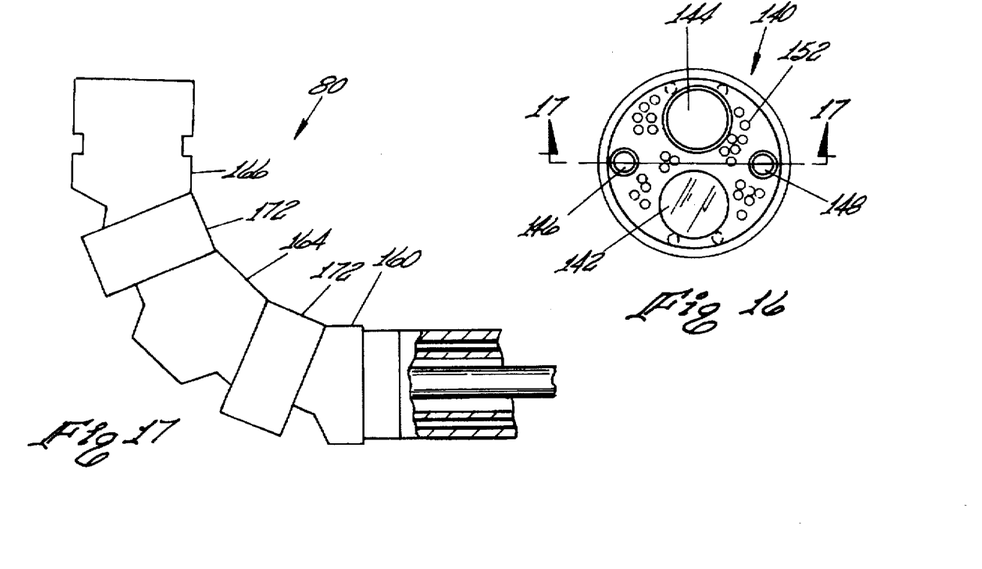
FIG. 16 is an end view of an endoscope utilizing the teachings of this invention having an image transfer system in the form of a fiber optic image bundle, a working channel, a plurality of irrigation/aspiration channels and fiber optic light guides.
FIG. 17 is a partial cross-sectional view taken along sectional lines 17—17 of FIG. 6 showing in partial cross-section the irrigation/aspiration channels and fiber optic image transfer system.

FIG. 16 shows that the endoscope could be used as an operating laparoscope 140. The operative laparoscope 140 would include image transfer system 142, a working channel 144, an irrigation channel 146, an aspiration channel 148 and fiber optic light guides 152.

FIG. 17 illustrates diagrammatically that the articulation mechanism 50 can be in the form of a robotic surgical finger. The robotic surgical finger would include a first thin walled element 160 which functions as a proximal ring in a manner similar to the first ring 54 as discussed in connection with FIGS. 5 through 7. The robotic surgical finger includes a first thin walled drive element 164 is operatively corrupted to the first thin walled element 160. Idle rings 172 would be disposed between the elements 160, 164 and 166 in an manner similar to the first idle rings 90 as shown in FIGS. 5 through 7. Element 164 functions as a central ring and element 166 functions as a distal ring.

Figure 18:
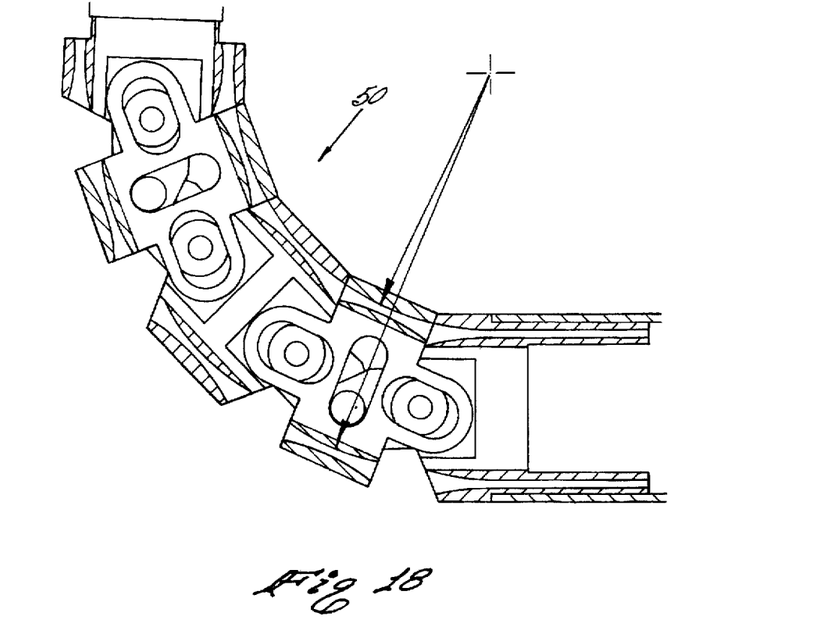
FIG. 18 is a diagrammatic representation of an articulation mechanism having a first ring, a first drive ring and a second drive ring wherein the first and second drive rings are adapted to cooperate with a first idle ring and a second idle ring.
Figure 19:
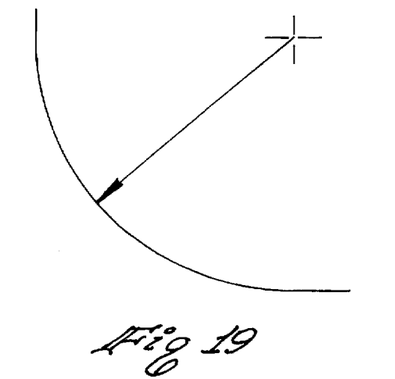
FIG. 19 is a diagrammatic representation of radius of curvature of the inner most surface of the drive and idle rings for approximately 90° deflection.
Figure 20:
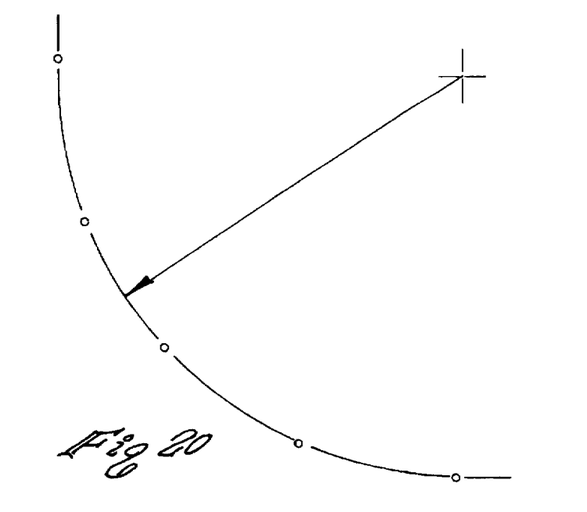
FIG. 20 is a diagrammatic representation of radius of curvature of the outer most surface of the drive and idle rings for approximately 90° deflection.

FIGS. 18, 19 and 20 illustrate the arcuate paths traversed by the articulation mechanism 50 during deflection.

Figure 21:
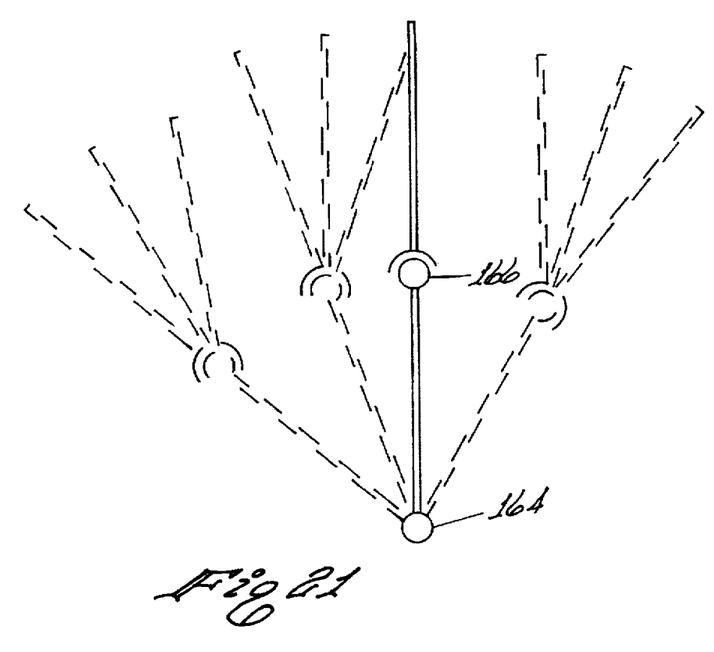
FIG. 21 is a pictorial representation of the deflection of a first drive ring and a second drive ring wherein the first drive ring is fixed at preselected positions and the second drive ring is moved over a plurality of positions.
Figure 22:
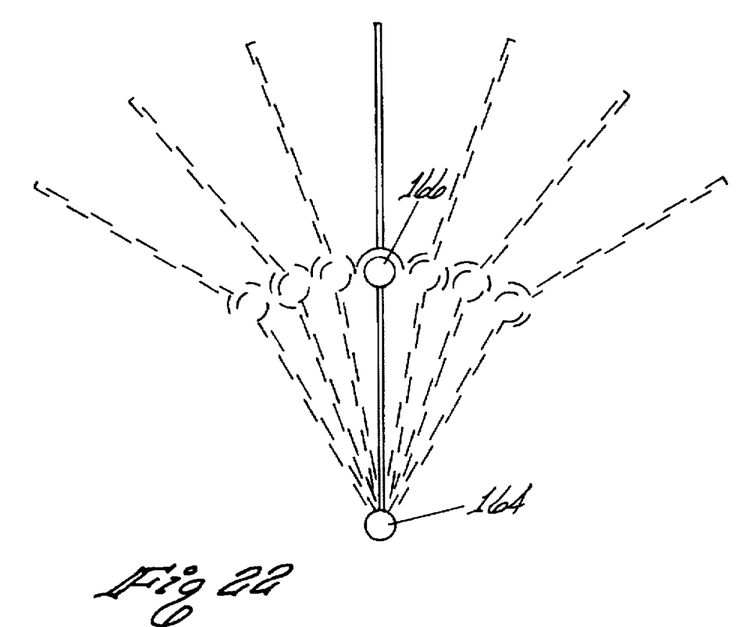
FIG. 22 is a pictorial representation of the deflection of a first drive ring and a second drive ring wherein the first drive ring and second drive ring are moved over a plurality of positions.

FIGS. 21 and 22 illustrate pictorially the movements of a robotic surgical finger wherein the first thin walled drive element 164 is fixed at predetermined positions and the second thin walled drive element 166 is deflected over a number of positions.

FIG. 22 illustrates that both the first thin walled drive element 164 and second thin walled drive element 166 are moveable over a plurality of positions.

FIGS. 21 and 22 further illustrate that the articulation mechanism can be formed or deflected into one or more angles and can form one or more shapes. Of course, the number of drive elements will determine the number of angles and the range of shapes which are achieved. Further, by using the teachings of the present invention, when the articulation mechanism is deflected over a predetermined angle or formed into a predetermined shape, the angle or shape will be retained independent of any exterior loading forces applied to the articulation mechanism. For example, if the articulation mechanism is used for lifting or pushing, the retarding force developed against the articulation mechanism will not change the angle or shape.

Figure 23:
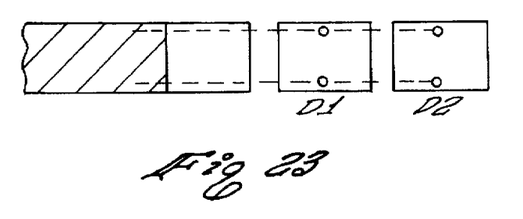
FIG. 23 is a pictorial representation of an articulation mechanism located at the distal end of an apparatus wherein the articulation mechanism has a first and second drive ring.

FIG. 23 illustrates pictorially that the articulation mechanism can have a minimum of two drive elements which are labeled D1 and D2 in order to provide deflection for the articulation mechanism over an arcuate path.

Figure 24:
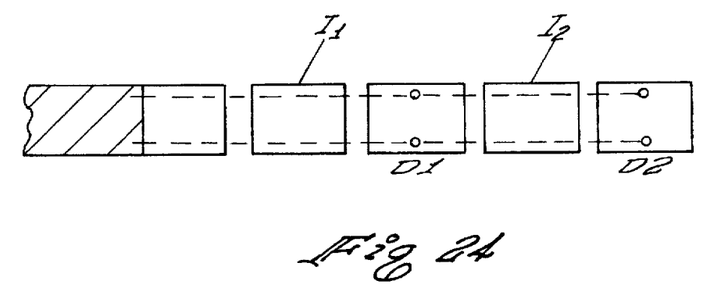
FIG. 24 is a pictorial representation of an articulation mechanism located at the distal end of an apparatus wherein the articulation mechanism has a first and second drive ring and two idle rings.

FIG. 24 illustrates pictorially that the articulation mechanism can have a minimum of two drive elements which are labeled D1 and D2 and a pair of idle rings shown as I1 and I2 in order to provide deflection for the articulation mechanism over an arcuate path.

Figure 25:
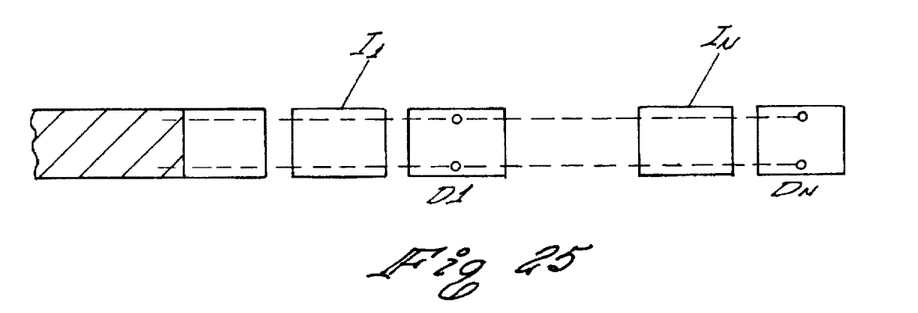
FIG. 25 is a pictorial representation of an articulation mechanism located at the distal end of an apparatus wherein the articulation mechanism has a first drive ring and an "N" drive ring and an "N" number of idle rings.

FIG. 25 illustrates pictorially that the articulation mechanism can have a minimum of N drive elements which are labeled D1 and DN and a pair of idle rings shown as I1 and IN in order to provide deflection for the articulation mechanism over an arcuate path.

Figure 26:
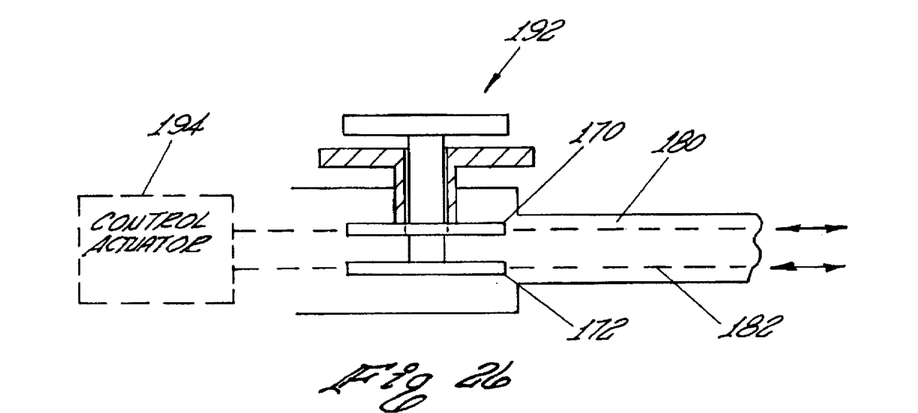
FIG. 26 is a pictorial representation of a cable driving mechanism for actuating each of a first and second pair of cables and a control means for programming said cable driving mechanism.

FIG. 26 illustrates pictorially that a driven member 170 and 172 which are operatively connected to cables 180 and 182 which are operatively connected to cables which are shown by dashed lines 180-182. The driven member can be operated either by a mechanical member 192 or by a control means such as a control actuator 194. The control acutuator 194 could be a computer controlled mechanism which precisely controls the movement of the driven members 170 and 172 to program transporting the cables 180 to 182 a predetermined distance and in a selected direction to position the articulation mechanism at locations along a respective arcuate path.

The preferred embodiment shown and described herein is directed for use in a medical procedure, preferably a TEE procedure. However, this is an exemplary use and it is envisioned that the principle and teaching herein could be adapted for other procedures as described herein. These procedures include other medical procedures, such as urological procedures, or industrial procedures.

What is claimed is:

1. An articulation mechanism comprising
a first ring adapted to be operatively connected to an end of a hollow elongated shaft of an apparatus, said first ring having a first fixed coupling member formed thereon and positioned in a spaced relationship to the end of said hollow elongated shaft, said first ring having an opening extending therethrough defining a throat between two configured surfaces forming opposed cable supporting surfaces adapted to pass a first pair of cables and a second pair of cables;

a first drive ring having fixed first and second actuation members positioned in a spaced opposed relationship and wherein one of said first and second actuation members is directly coupled to said first fixed coupling member, said first drive ring including a first outer edge and a second outer edge defining a throat between two configured surfaces forming opposed cable supporting surfaces adapted to pass said first pair of cables and said second pair of cables, said first drive member further including a first cable connecting member for operatively connecting said first drive ring to said first pair of cables, said first drive ring being capable of pivoting relative to said first ring in response to the direction of movement of the first pair of cables to move said first drive ring over a first arcuate path urging the cables rigidly against the cable opposing surfaces; and a second drive ring having a second fixed coupling member formed thereon which is directly coupled to the other of said first and second actuation members, said second drive ring including an opening extending therethrough defining a throat between two configured surfaces forming opposed cable supporting surfaces adapted to pass said second pair of cables, said second drive ring further including a second cable connecting member for operatively connecting to said second drive ring said second pair of cables, said second drive ring being capable of pivoting relative to said first drive ring in response to a movement of said second pair of cables to move said second drive ring over a second arcuate path which is co-planar with the first arcuate path urging the cables rigidly against the cable opposing surfaces.

2. The articulation mechanism of claim 1 further comprising
a first single idle ring directly pivotally coupled between the first coupling member of said first ring and said one of the first and second actuation members of said first drive ring;
said first single idle ring including a first outer edge and a second outer edge defining a throat between two configured surfaces forming opposed cable supporting surfaces adapted to pass said first pair of cables and said second pair of cables.

3. The articulation mechanism of claim 2 further comprising
a second single idle ring directly pivotally coupled between the second coupling member of said second drive ring and said other of said first and second actuation members of said first drive ring;
said second single idle ring having a first outer edge and a second outer edge defining a throat between two configured surfaces forming opposed cable supporting surfaces adapted to pass said second pair of cables for urging the cables rigidly against the cable opposing surfaces forming a rigid member.

4. A robotic surgical finger for an endoscope comprising
a first thin walled element having an opening extending axially therethrough fixedly operatively connected to the distal end of an endoscope, said first element having a first fixed coupling member formed thereon and positioned in a spaced relationship to the end of said endoscope, said first thin walled element having an opening extending therethrough defining a throat between two configured surfaces forming opposed cable supporting surfaces adapted to pass a first pair of actuatable cables and a second pair of actuatable cables;

a first thin walled drive element having an opening extending axially therethrough defining a throat between two configured sections forming opposed cable supporting surfaces adapted to pass said first pair of actuatable cables and said second pair of cables, said first thin walled drive element further including fixed first and second actuation members positioned in a spaced opposed relationship and wherein one of said first and second actuation members is directly pivotally coupled to said first fixed coupling member, said first drive element including a first cable connecting member for operatively connecting said first thin walled drive element to said first pair of actuatable cables for pivoting said first thin walled drive element over a first arcuate path in response to actuation of said first pair of cables; and a second thin walled drive element having an opening extending axially therethrough defining a throat between two configured surfaces forming opposed cable supporting surfaces adapted to pass said second pair of actuatable cables, said second thin walled drive element further including a second fixed coupling member formed thereon which is directly pivotally coupled to the other of said first and second actuation members, said second thin walled drive element including a second cable connecting member for attaching said second thin walled drive element to said second pair of actuatable cables for pivoting in response to the actuation of said second pair of cables to move said second thin walled drive element over a second arcuate path which is co-planar with the first arcuate path urging the cables rigidly against the cable opposing surfaces forming a rigid member.

5. The robotic surgical finger of claim 4 further comprising a first thin walled single idle ring directly pivotally coupled between the first fixed coupling member of said first thin walled element and one of said first and second actuation members of said first thin walled drive element;

said first thin walled single idle ring including an opening extending axially therethrough defining a throat between two configured surfaces forming opposed cable supporting surfaces for slideable receiving and supporting a first pair of actuatable and for urging the cables rigidly against the cable opposing surface forming a rigid member.

6. The robotic surgical finger of claim 5 further comprising a second thin walled single idle ring directly pivotally coupled between the other of said first and second actuation members of said first thin walled drive element and the second fixed coupling member of said second thin walled drive element;

said second thin walled idle ring including a first outer edge and a second outer edge therethrough defining a throat between two configured surfaces forming opposed cable supporting surfaces adapted to pass said second pair of cables for urging the cables rigidly against the cable opposing surfaces forming a rigid member.

7. An articulation mechanism for an endoscope, said endoscope including a generally elongated hollow shaft having a proximal end and a distal end, said elongated hollow shaft having a control head located at the proximal and thereof for moving pairs of cables extending from the proximal and thereof to the articulation mechanism located at the distal end thereof, said articulation mechanism comprising a proximal ring having a first actuation member and a second actuation member with one of said first actuation member and said second actuation member fixedly operatively connected to the distal end of the elongated hollow shaft, said proximal ring defining a first fixed coupling member, said proximal ring having an opening extending therethrough defining a throat between two configured surfaces forming opposed cable supporting surfaces adapted to pass a first pair of cables and a second pair of cables, said proximal ring including a first cable connecting member for operatively connecting said proximal ring to said first pair of cables for pivoting in response to the direction of movement of the first pair of cables over a first arcuate path urging the cables rigidly against the cable opposing surfaces;

a central ring having an opening extending therethrough defining a throat between two configured surfaces forming opposed cable supporting surfaces adapted to pass said second pair of cables, said central ring further including first and second fixed elongated support members wherein one of the elongated support members is directly coupled to said first fixed coupling member and enables the central ring to pivot relative to said first fixed coupling member, said central ring including a first cable connecting member for operatively connecting said central ring to said first pair of cables for pivoting in response to the direction of movement of the first pair of cables over a first arcuate path urging the cables rigidly against the cable opposing surfaces; and a distal ring having an opening extending therethrough defining a throat between two configured surfaces forming opposed cable supporting surfaces adapted to pass a second pair of cables, said distal ring further including a second fixed coupling member which is directly coupled to and enables the distal ring to pivot relative to the other of said elongated support members, said distal ring including a second cable connecting member for operatively connecting said distal ring to said second pair of cables for pivoting in response to the direction of movement of the second pair of cables over a first arcuate path urging the cables rigidly against the cable opposing surfaces;

said central ring and said distal ring being responsive to its associated cable pair being transported in a first direction to pivot and support the central ring including its elongated support members and the distal ring over a first predetermined angular path within a plane and being responsive to its associated cable pair being transported in a second opposite direction to pivot and support the central ring including its elongated support members and the distal ring over a second predetermined angular path substantially in the same plane, said articulation mechanism sweeping the other of said first outer edge and second outer edge of the distal ring over an arcuate planar path defined by said first predetermined angular path and said second predetermined angular path.

8. The articulation mechanism of claim 7 further comprising a first idle ring defining first and second elongated support members, one of said elongated support members being directly pivotally coupled to one of the elongated support members of said central ring and the other of said elongated support members being directly pivotally operatively coupled to at least one of the first fixed coupling member of said proximal ring and the second fixed coupling member of said distal ring, said first idle ring defining a throat between two configured surfaces forming opposed cable supporting surfaces adapted to pass said first pair of cables and said second pair of cables.

9. The articulation member of claim 8 further comprising a second idle ring defining first and second elongated support members, one of said elongated support members being directly pivotally operatively coupled to the other of the elongated support members of said central ring and the other of said elongated support members being directly pivotally operatively coupled to the second fixed coupling member of said distal ring, said second idle ring defining a throat between two configured surfaces forming opposed cable supporting surfaces adapted to pass said second pair of cables.

10. An endoscope having an articulation mechanism comprising a generally elongated shaft having a proximal end and a distal end;

a control head operatively coupled to the proximal end of said elongated shaft, said control head including a cable driving mechanism;

an articulation mechanism including a proximal ring having a first actuation member and a second actuation member with one of said first actuation member and said second actuation member fixedly directly coupled to the distal end of the elongated shaft, the other of said first actuation member and said second actuation member of said proximal ring defining a first fixed coupling member, said proximal ring having an opening extending therethrough defining a throat between two configured surfaces forming opposed cable supporting surfaces adapted to pass a first pair of cables and a second pair of cables, said proximal ring including a first cable connecting member for operatively connecting said proximal ring to said first pair of cables for pivoting in response to the direction of movement of said first pair of cables over a first arcuate path urging the cables rigidly against the cable opposing surfaces;

a central ring having a first outer edge and a second outer edge, said central ring having an opening extending therethrough defining a throat between two configured surfaces forming opposed cable supporting surfaces adapted to pass said second pair of cables, said central ring further including a fixed elongated support members wherein one of the elongated support members is directly coupled to said first fixed coupling member and enables the central ring to pivot relative to said first fixed coupling member;

a distal ring having a first outer edge and a second outer edge, said distal ring having an opening extending therethrough defining a throat between two configured surfaces forming opposed cable supporting surfaces adapted to pass said a second pair of cables, said distal ring further including a second fixed coupling member which is directly coupled to and enables the distal ring to pivot relative to the other of said elongated support members; and said central ring and said distal ring being responsive to its associated cable pair being transported in a first direction to pivot and support the central ring including its elongated support members and the distal ring over a first predetermined angular path within a plane and being responsive to its associated cable pair being transported in a second opposite direction to pivot and support the central ring including its elongated support members and the distal ring over a second predetermined angular path substantially in the same plane, said articulation mechanism sweeping the other of said first outer edge and second outer edge of the distal ring over an arcuate planar path defined by said first predetermined angular path and said second predetermined angular path urging the cables rigidly against the cable opposing surfaces; and at least two pair of cables extending from the control head to the articulation mechanism, one of said two pair of cables being connected by the first cable connecting member to the proximal ring and the other of said two pair of cables being connected by the second cable connector member to the distal ring.

11. The endoscope of claim 10 wherein the endoscope has a proximal end and further comprises an image transfer system located with the endoscope and extending from the proximal end thereof and through the articulation mechanism to view an operative site adjacent the articulation mechanism and transfer an image thereof to the proximal end of the endoscope.

12. The endoscope of claim 10 wherein the endoscope has a proximal end further comprising an ultrasound transducer operatively mounted within the articulation mechanism and adapted to be transported over the arcuate paths by the articulation mechanism adjacent to an operative site to produce an ultrasound image thereof;

an electrical conductor located within the endoscope and extending from the proximal end thereof to the ultrasound transducer, said electrical conductor being operatively connected to said ultrasound transducer to receive electrical signals representative of an ultrasound image.

13. A robotic finger mechanism for a working instrument comprising a first thin walled element having an opening extending axially therethrough fixedly operatively connected to the distal end of an instrument, said first element having a first fixed coupling member formed thereon and positioned in a spaced relationship to the end of said instrument, said first thin walled element having an opening extending therethrough defining a throat between two configured surfaces forming opposed cable supporting surfaces adapted to pass a first pair of actuatable cables and a second pair of actuatable cables;

a first thin walled drive element having an opening extending axially therethrough, said first thin walled drive element having an opening extending therethrough defining a throat between two configured surfaces forming opposed cable supporting surfaces adapted to pass said first pair of actuatable cables and said second pair of actuatable cables, said first thin walled drive element further including and first and second elongated support members positioned in a spaced opposed relationship and wherein one of said first and second elongated support members is directly coupled to said first fixed coupling member to enable rotational movement therebetween, said first drive element including a first cable connecting member for operatively connecting said first thin walled drive element to said first pair of actuatable cables for rotating in response to actuation of said first pair of actuatable cables to move said first drive element over a first arcuate path urging the cables rigidly against the cable opposing surfaces; and a second thin walled drive element having an opening extending axially therethrough, said second thin walled drive element having an opening extending therethrough defining a throat between two configured surfaces forming opposed cable supporting surfaces adapted to pass said second pair of actuatable cables, said first thin walled drive element further including a second fixed coupling member formed thereon which is coupled to the other of said first and second elongated support members to enable rotational movement therebetween, said second drive element including a second cable connecting member for directly connecting said second thin walled drive element to said second pair of actuatable cables for rotating in response to the actuation of a second pair of cables to move said second drive element over a second arcuate path which is co-planar with the first arcuate path.

14. The robotic finger mechanism of claim 13 further comprising a first thin walled idle ring directly coupled between the first fixed coupling member of said first thin walled element and said one of said first and second elongated support members of said first thin walled drive element to enable rotational movement therebetween;

said first thin walled idle ring including at least two pair of spaced curved openings extending therethrough for slideably receiving and supporting a first and second pair of actuatable cables.

15. The robotic finger mechanism of claim 14 further comprising a second thin walled idle ring directly coupled between the other of said first and second elongated support members of said first thin walled drive element and the second coupling member of said second drive element to enable rotational movement therebetween;

said second thin walled idle ring including an outer wall having at least two pair of spaced curved openings extending therethrough for slideably receiving and supporting said second pair of cables.

16. An instrument having a robotic articulation mechanism wherein said instrument includes a generally elongated shaft having a proximal end and a distal end, said shaft having a control head located at the proximal end thereof for moving pairs of cables extending from the proximal end thereof to the robotic articulation mechanism located at the distal end thereof, said robotic articulation mechanism comprising a first thin walled element having an opening extending axially therethrough fixedly operatively connected to the distal end of said elongated shaft, said first element having a first fixed coupling member formed thereon and positioned in a spaced relationship to the end of said instrument, said first thin walled element having an opening extending therethrough defining a throat between two configured surfaces forming opposed cable supporting surfaces adapted to pass a first pair of actuatable cables and a second pair of actuatable cables;

a first thin walled drive element having an opening extending axially therethrough, said first thin walled drive element having an opening extending therethrough defining a throat between two configured surfaces forming opposed cable supporting surfaces adapted to pass said first pair of actuatable cables and said second pair of actuatable cables, said first thin walled drive element further including first and second elongated support members positioned in a spaced opposed relationship and wherein one of said first and second elongated support members is directly coupled to said first fixed coupling member to enable rotational movement therebetween, said first thin walled drive element including a first cable connecting member for operatively connecting said first thin wall drive element to a first pair of actuatable cables for rotating in response to actuation of said first pair of actuatable cables to move said first thin walled drive element over a first arcuate path; and a second thin walled drive element having an opening extending axially therethrough, said second thin walled element having an opening extending therethrough defining a throat between two configured surfaces forming opposed cable supporting surfaces adapted to pass said second pair of actuatable cables, said second thin walled drive element further including a second fixed coupling member formed thereon which is directly coupled to the other of said first and second elongated support members to enable rotational movement therebetween, said second drive element including a second cable connecting member for directly connecting said second drive element to said second pair of actuatable cables for rotating in response to the actuation of a second pair of actuatable cables to move said second thin walled drive element over a second arcuate path which is co-planar with the first arcuate path.

17. The instrument of claim 16 wherein said robotic articulation mechanism further comprises a first thin walled idle ring having a first outer edge and a second outer edge defining a throat between two configured surfaces forming opposed cable supporting surfaces adapted to pass said first pair of actuatable cables and said second pair of actuatable cables, said first thin walled idle ring defining first and second elongated support members, one of said elongated support members being directly coupled between the first fixed coupling member of said first thin walled element to enable rotational movement therebetween and the other of said elongated support members being operatively coupled to said one of the first and second elongated support members of said first thin walled drive elements to enable rotational movement therebetween;

a second thin walled idle ring having a first outer edge and a second outer edge, said second thin walled idle ring having an opening extending therethrough defining a throat between two configured surfaces forming opposed cable supporting surfaces adapted to pass said second pair of actuatable cables, said thin walled idle ring defining first and second elongated support members, one of said elongated support members being directly coupled between the other of the first and second elongated support members of said first thin walled drive member and the other of said elongated support member being directly coupled to the second fixed coupling member of said second thin walled drive element, said second thin walled idle ring including an outer wall having one pair of spaced curved openings extending therethrough for slideably receiving and supporting only a second pair of actuatable cables.

18. The instrument of claim 16 having a robotic articulation mechanism wherein the control head further comprises a cable driving mechanism for actuating each of a first and second pair of actuatable cables; and a control means for programming said cable driving mechanism to actuate each of said first and second actuatable cables to move a selected distance in a selected direction to controllably deflect said first and second thin walled drive elements over said first and second arcuate path.

19. The instrument of claim 16 wherein said control means comprises
- a drive member having a first and second coacting member; and
- a driven member operatively coupled to a first and second pair of actuatable cables and wherein said driven member includes a first and second reactive member which coacts with said first and second coacting member, said driven member being responsive to the drive member to transport at least one of the first and second pair of actuatable cables a predetermined distance in a selected direction to rotate the drive element over its associated arcuate path.

20. The instrument of claim 19 wherein each said first and second co-acting members are a drive gear and each of the first and second reactive members is a linear geared rack member which is driven by rotation of the drive gear.

21. The instrument of claim 19 wherein said control means further comprises
- a controlled actuator operatively connected to said drive member for controlling movement of said first and second coacting members to program transporting of each of a first and second actuatable cable pair a predetermine distance and in a selected direction to position said first and second drive elements at locations along its respective arcuate path.

* * * * *